(12) United States Patent
Ladet

(10) Patent No.: US 9,855,372 B2
(45) Date of Patent: *Jan. 2, 2018

(54) AUTO-SEALANT MATRIX FOR TISSUE REPAIR

(75) Inventor: Sébastien Ladet, Lyons (FR)

(73) Assignee: SOFRADIM PRODUCTION, Trevoux (FR)

( * ) Notice: Subject to any disclaimer, the term of this patent is extended or adjusted under 35 U.S.C. 154(b) by 1168 days.

This patent is subject to a terminal disclaimer.

(21) Appl. No.: 13/124,163

(22) PCT Filed: Oct. 16, 2009

(86) PCT No.: PCT/IB2009/007510
§ 371 (c)(1),
(2), (4) Date: Jul. 1, 2011

(87) PCT Pub. No.: WO2010/043979
PCT Pub. Date: Apr. 22, 2010

(65) Prior Publication Data
US 2011/0251699 A1    Oct. 13, 2011

Related U.S. Application Data

(60) Provisional application No. 61/196,544, filed on Oct. 17, 2008.

(51) Int. Cl.
*A61L 31/14* (2006.01)
*A61L 31/04* (2006.01)

(52) U.S. Cl.
CPC ........... *A61L 31/146* (2013.01); *A61L 31/044* (2013.01); *A61L 31/145* (2013.01)

(58) Field of Classification Search
None
See application file for complete search history.

(56) References Cited

U.S. PATENT DOCUMENTS

| 4,931,546 A * | 6/1990 | Tardy et al. .................. 530/356 |
| 5,024,841 A | 6/1991 | Chu et al. |
| 5,201,745 A | 4/1993 | Tayot et al. |
| 5,480,436 A * | 1/1996 | Bakker et al. .................. 600/37 |
| 2001/0003126 A1* | 6/2001 | Rhee et al. .................. 525/54.1 |
| 2001/0016205 A1 | 8/2001 | Shimizu |
| 2002/0022883 A1 | 2/2002 | Burg |
| 2002/0106409 A1* | 8/2002 | Sawhney et al. ............. 424/484 |
| 2003/0031697 A1 | 2/2003 | Chudzik et al. |
| 2005/0042265 A1* | 2/2005 | Guillot et al. ................ 424/445 |
| 2005/0232979 A1 | 10/2005 | Shoshan |

FOREIGN PATENT DOCUMENTS

| WO | WO 01/54735 | 8/2001 |
| WO | WO 2006/022671 | 3/2006 |

OTHER PUBLICATIONS

Lee, Jong Eun, et al., Biomaterials, 25 (2004) pp. 4163-4173.*
Lovisetto, Federico, et al., Ann Surf, 245 (2007), pp. 222-231.*
International Search Report PCT/IB2009/007510 dated Apr. 12, 2010.
European Search Report dated Apr. 8, 2013 in corresponding European Patent Application No. 12175759; 2 pages.
Canadian Office Action dated Sep. 26, 2016 in corresponding Canadian Patent Application No. 2,740,596, 3 pages.
Canadian Office Action dated Oct. 30, 2015 in corresponding Canadian Patent Application No. 2,740,596, 6 pages.

* cited by examiner

*Primary Examiner* — Dennis J Parad
*Assistant Examiner* — Lyndsey Beckhardt

(57) ABSTRACT

Implants for tissue repair/regeneration include a porous layer combined with dry materials that are activated to form a hydrogel upon contact with aqueous physiological fluids.

9 Claims, 7 Drawing Sheets

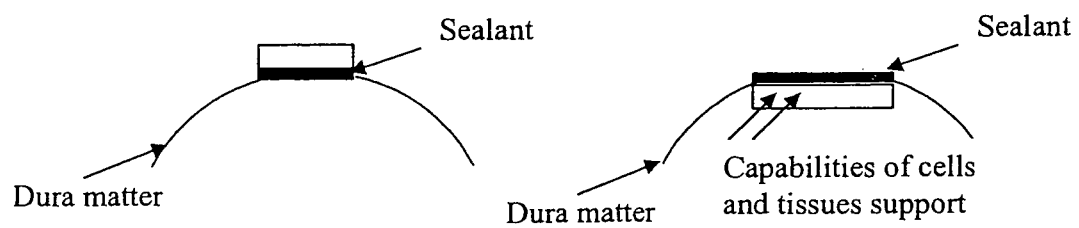
Figure 9A                    Figure 9B

AUTO-SEALANT MATRIX FOR TISSUE REPAIR

CROSS-REFERENCE TO RELATED APPLICATIONS

This application is a U.S. National Stage Application filed under 35 U.S.C. §371(a) of International Application No. PCT/IB2009/007510 filed Oct. 16, 2009, which claims the benefit of and priority to U.S. Provisional Application Ser. No. 61/196,544 filed Oct. 17, 2008, the entire contents of which are incorporated by reference herein.

BACKGROUND

Dura mater closure has mainly focused on the used of a dural substitute, a sealant or a combination of both substitute and sealant in order to prevent cerebrospinal fluid ("CSF") leakage. Dural substitutes based on collagen matrices provide a good bioresorbable and safe substitute, compared to xenograft or allograft implants. Nevertheless, dural substitutes based on collagen matrices have inferior watertight properties to prevent cerebrospinal fluid ("CSF") leakage, short persistence and low suture retention for use in infratentorial or spine areas. Synthetic dural substitutes usually show good mechanical and watertight properties, but generally are not absorbable, show a lack of conformability and are less easy to use since they always require suturing.

SUMMARY

Implantable, sealing dural substitutes described herein include a polymer matrix to support tissue regeneration while providing high suture retention and a controlled and desirable time of in vivo resorption, combined with dry materials that are activated by the presence of aqueous physiological fluids. When implanted at the site of a dural defect the dry materials of the present dural substitutes are activated by the body fluids to induce in situ formation of a hydrogel providing both stickiness and sealing properties to the implant. The combination of matrix with dry materials ensures an easy way to stick, seal and regenerate the dura mater in an all in one product.

An aspect of the invention of the present disclosure is an implant comprising:
a porous layer,
a first hydrogel precursor,
a second hydrogel precursor,
optionally one or more additional layers, wherein
said first hydrogel precursor is present in a layer selected from said porous layer and said one or more additional layers, and
said second hydrogel precursor is present in a layer selected from said porous layer and said one or more additional layers.
In other words, an aspect of the invention is an implant having at least one of the following structures:
  i) A structure comprising a porous layer, a first hydrogel precursor, a second hydrogel precursor, wherein said first hydrogel precursor and said second hydrogel precursor are present in said porous layer, or
  ii) A structure comprising a porous layer and one or more additional layers, wherein
said first hydrogel precursor is present in a layer selected from said porous layer and said one or more additional layers, and
said second hydrogel precursor is present in a layer selected from said porous layer and said one or more additional layers.

In case of structure i) above, the porous layer may comprise two or more sublayers.

In embodiments, the first hydrogel precursor has nucleophilic functional groups, such as amines, the second hydrogel precursor having electrophilic functional groups, such as N-hydroxysuccinimides.

In embodiments, the first hydrogel precursor is tri-lysine and the second hydrogel precursor is PEG-succinimidyl glutarate.

In embodiments, said porous layer comprises a self-crosslinked compound of a functionalized collagen and a glycosaminoglycan. In embodiments, the glycosaminoglycan is chitosan. In embodiments, the glycosaminoglycan displays a degree of acetylation of about 1% to about 50%, preferably of 2.5%.

The functionalized collagen may be oxidized collagen.

In embodiments, said first hydrogel precursor is present in said porous layer. In such embodiments, the porous layer may comprise a first sublayer comprising the first hydrogel precursor and a second sublayer free from hydrogel precursor. The implant may further comprise a first additional layer, said first additional layer being a non porous layer comprising said second hydrogel precursor.

Said first additional layer may be applied to the second sublayer free from hydrogel precursor.

The implant may further comprise a second additional layer, said second additional layer being a non porous layer free of hydrogel precursor, located between said porous layer and said first additional layer.

In embodiments, the porous layer further comprises a third sublayer comprising the second hydrogel precursor, said third sublayer being adjacent said second sublayer. In such embodiments, the implant may be free of any additional layer.

In embodiments, the first hydrogel precursor is spatially separated from the second hydrogel precursor.

Alternatively, the implant may further comprise a first additional layer and a second additional layer, said first hydrogel precursor being present in a layer selected from said porous layer and said first additional layer, said second hydrogel precursor being present in said second additional layer, said first additional layer being a non porous layer. For example, in such embodiments, said first additional layer is sandwiched between said porous layer and said second additional layer.

Said first hydrogel precursor may be present in said first additional layer, said first additional layer being a dry non porous layer.

Another aspect of the present invention is a method for preparing the implant above, wherein the porous layer is obtained by freeze-drying a polymer solution comprising one or more biodegradable and biocompatible polymers. The first hydrogel precursor may be incorporated in said polymer solution before freeze-drying. Said polymer solution may comprise a mixture of a functionalized collagen, for example non heated, oxidized collagen, and of a glycosaminoglycan, for example chitosan.

The following clauses 1-61 define aspects of the invention: 1. An implant comprising:
a porous layer comprising (a) a self-crosslinked compound of a functionalized collagen and a glycosaminoglycan and (b) a first hydrogel precursor; and
a film containing a second hydrogel precursor applied to the porous layer.

2. An implant comprising
a porous layer comprising a self-crosslinked compound of a functionalized collagen and a glycosaminoglycan,
the porous layer having a first portion comprising a first hydrogel precursor and a second portion comprising a second hydrogel precursor,
the first portion of the porous layer being spatially separated from the second portion of the porous layer.

3. An implant as in either of clauses 1 or 2, wherein the glycosaminoglycan is chitosan.

4. An implant as in either of clauses 1 or 2, wherein the glycosaminoglycan displays a degree of acetylation of about 1% to about 50%.

5. An implant as in either of clauses 1 or 2, wherein the porous layer comprises a functionalized collagen self-crosslinked to a first glycosaminoglycan and to a second glycosaminoglycan, the first glycosaminoglycan having a first degree of acetylation and the second glycosaminoglycans having a second degree of acetylation different from the first degree of acetylation.

6. An implant as in any of clauses 1-5, wherein the functionalized collagen is oxidized collagen.

7. An implant as in any of clauses 1-5, wherein the functionalized collagen is denatured, oxidized collagen.

8. An implant as in any of clauses 1-7, wherein the porous layer further comprises glycerine.

9. An implant in any of clauses 1-8, wherein the porous layer further comprises a bioactive agent.

10. An implant as in any of clauses 1-9, wherein the porous layer has a thickness of from about 0.2 mm to about 1 cm.

10. An implant as in clause 1 wherein the porous layer comprises a first portion comprising the first hydrogel precursor and a second portion free from hydrogel precursor.

11. An implant comprising:
a porous layer;
a first film containing a first hydrogel precursor applied to a first surface of the porous layer; and
a second film containing a second hydrogel precursor applied to a second surface the porous layer.

12. An implant as in clause 11 wherein the porous layer comprises a self-crosslinked compound of a functionalized collagen and a glycosaminoglycan.

13. An implant comprising:
a porous layer having a first portion comprising a first hydrogel precursor and a second portion free from hydrogel precursor; and
a film containing a second hydrogel precursor applied to the second portion free from hydrogel precursor.

14. An implant as in clause 13 wherein the porous layer comprises a self-crosslinked compound of a functionalized collagen and a glycosaminoglycan.

15. An implant as in clause 13 further comprising a non-porous layer containing no hydrogel precursor applied to a second surface of the porous layer.

16. An implant as in clause 15 wherein the non-porous layer comprises at least about 40 percent by weight collagen.

17. An implant comprising:
a porous layer;
a first film applied to a first surface of the porous layer, the first film comprising a first hydrogel precursor; and
a second film containing a second hydrogel precursor applied to the first film.

18. An implant comprising:
a porous layer comprising a first hydrogel precursor;
a first film containing no hydrogel precursor applied to a first surface of the porous layer; and
a second film comprising a second hydrogel precursor applied to the first film.

19. A method of treating a dural defect comprising providing an implant as in any of clauses 1-18; and
implanting implant at the site of a dural defect.

20. A method comprising
preparing a porous layer comprising (a) a self-crosslinked compound of a functionalized collagen and a glycosaminoglycan and (b) a first hydrogel precursor; and
applying a film comprising a second hydrogel precursor to the porous layer.

21. A method comprising
at least partially gelling a first solution comprising a first hydrogel precursor;
applying a second solution directly onto the at least partially gelled first solution; and
lyophilizing the first and second solution to provide a first porous sublayer containing the first hydrogel precursor secured to a second porous sublayer.

22. A method as in clause 21 wherein at least one of the first solution or the second solution comprises a compound containing collagen chemically cross-linked to a glycosaminoglycan.

23. A method as in clause 21 wherein at least one of the first solution or the second solution comprises a self-cross-linked compound of a functionalized collagen and a glycosaminoglycan 24. A method as in clause 21 wherein at least one of the first solution or the second solution comprises oxidized collagen.

25. A method as in clause 21 wherein the second solution comprises a second hydrogel precursor.

26. A method as in clause 21 further comprising applying a film to the second porous sublayer, the film comprising a second hydrogel precursor.

27. A method as in clause 21 further comprising applying a third solution directly onto the second solution prior to lyophilizing, wherein the second solution has a first viscosity and the third solution has a second viscosity that is lower than the first viscosity.

28. A method as in clause 27 further comprising at least partially gelling the second solution and applying a third solution directly onto the second layer prior to lyophilizing.

29. A method as in clause 27 wherein the third solution comprises a second hydrogel precursor.

30. A method as in clause 21 further comprising freezing the first and second solution and applying a third solution directly onto the second layer prior to lyophilizing.

31. A method as in clause 30 wherein the third solution comprises a second hydrogel precursor.

32. A method comprising
providing a layer of a first solution containing a first hydrogel precursor, the first solution having a first viscosity;
applying a layer of a second solution directly onto the layer of a first solution, the second solution having a viscosity lower than the viscosity of the first solution; and
lyophilizing the first and second solution to provide a first porous sublayer containing the first hydrogel precursor secured to a second porous sublayer.

33. A method as in clause 32 wherein at least one of the first solution or the second solution comprises a compound containing collagen chemically cross-linked to a glycosaminoglycan.

34. A method as in clause 32 wherein at least one of the first solution or the second solution comprises a self-cross-linked compound of a functionalized collagen and a glycosaminoglycan 35. A method as in clause 32 wherein at least one of the first solution or the second solution comprises oxidized collagen.

36. A method as in clause 32 wherein the second solution comprises a second hydrogel precursor.

37. A method as in clause 32 further comprising applying a film to the second porous sublayer, the film comprising a second hydrogel precursor.

38. A method as in clause 32 further comprising applying a third solution directly onto the second solution prior to lyophilizing, wherein the third solution has a viscosity that is lower than the viscosity of the second solution.

39. A method as in clause 38 wherein the third solution comprises a second hydrogel precursor.

40. A method as in clause 32 further comprising at least partially gelling the first and second solutions and applying a third solution directly onto the second layer prior to lyophilizing.

41. A method as in clause 40 wherein the third solution comprises a second hydrogel precursor.

42. A method as in clause 32 further comprising freezing the first and second solutions and applying a third solution directly onto the second layer prior to lyophilizing.

43. A method as in clause 42 wherein the third solution comprises a second hydrogel precursor.

44. A method comprising
freezing a first solution comprising a first hydrogel precursor;
applying a second solution directly onto the frozen first solution; and
lyophilizing the first and second solution to provide a first porous sublayer comprising the first hydrogel precursor secured to a second porous sublayer.

45. A method as in clause 44 wherein the first solution comprises a compound containing collagen chemically cross-linked to a glycosaminoglycan.

46. A method as in clause 44 wherein the first solution comprises a self-crosslinked compound of a functionalized collagen and a glycosaminoglycan 47. A method as in clause 44 wherein the second solution comprises a compound containing collagen chemically cross-linked to a glycosaminoglycan.

48. A method as in clause 44 wherein the second solution comprises a second hydrogel precursor.

49. A method as in clause 44 further comprising applying a film to the second porous sublayer, the film comprising a second hydrogel precursor.

50. A method as in clause 44 further comprising applying a third solution directly onto the second solution prior to lyophilizing, wherein the third solution has a viscosity that is lower than the viscosity of the second solution.

51. A method as in clause 50 wherein the third solution comprises a second hydrogel precursor.

52. A method as in clause 44 further comprising at least partially gelling the first and second solutions and applying a third solution directly onto the second layer prior to lyophilizing.

53. A method as in clause 52 wherein the third solution comprises a second hydrogel precursor.

54. A method as in clause 44 further comprising freezing the second solution and applying a third solution directly onto the frozen second layer prior to lyophilizing.

55. A method as in clause 54 wherein the third solution comprises a second hydrogel precursor.

56. A method comprising
at least partially gelling a first solution containing a first hydrogel precursor;
applying a second solution containing no hydrogel precursor directly onto the at least partially gelled first solution;
at least partially gelling the second solution;
applying a third solution containing a second hydrogel precursor directly onto the at least partially gelled second solution; and
lyophilizing the first, second and third solutions to provide a first porous sublayer comprising the first hydrogel precursor secured to a second porous sublayer comprising the second hydrogel precursor via an intermediate porous sublayer containing no hydrogel precursor.

57. A method as in clause 56 wherein at least one of the first solution, the second solution or the third solution comprises a compound containing collagen chemically cross-linked to a glycosaminoglycan.

58. A method as in clause 56 wherein at least one of the first solution, the second solution or the third solution comprises a compound containing collagen self cross-linked to a glycosaminoglycan 59. A method as in clause 56 wherein at least one of the first solution, the second solution or the third solution comprises oxidized collagen.

60. A method comprising
contacting a porous layer comprising (a) a self-crosslinked compound of a functionalized collagen and a glycosaminoglycan and (b) a first hydrogel precursor with a first surface of a first, at least partially gelled solution containing no hydrogel precursor; and
applying a second solution comprising a second hydrogel precursor to a second surface of the first, at least partially gelled solution containing no hydrogel precursor.

61. An implant comprising
a first porous sublayer comprising a first hydrogel precursor secured to a second porous sublayer comprising a second hydrogel precursor via an intermediate porous sublayer containing no hydrogel precursor.

BRIEF DESCRIPTION OF THE DRAWINGS

FIGS. 9A and B schematically illustrate use of implants in accordance with embodiments of the present disclosure over small and large tissue defects, respectively.

DETAILED DESCRIPTION OF PREFERRED EMBODIMENTS

According to the present description, the expressions "porous layer" and "porous matrix" have the same meaning and both designate a porous layer. By "porous layer" is meant, according to the present description, a layer having pores, voids, holes, channels, favourable to cell colonization. For example, the porous layer may be a sponge or a foam.

By "non porous layer", is meant, according to the present description, a layer being substantially free of any pores and having a substantially even surface, not favourable to cell colonization. For example, the non porous layer may be a film.

According to the present description, the expressions "implant", "sealant tissue patch", "sealant patch", "patch", "substitute" have the same meaning and all designate the implant of the present application.

The present sealant tissue patch can include one or more layers, in embodiments at least one of the layers including dry components that, when contacted by physiological fluids, combine to form a hydrogel. Thus, the present sealant tissue patch is self-sticking and sealing. In embodiments, the present sealant tissue patch is fully bioresorbable. The sealant tissue patch implant is intended for use in any procedure where the repair or substitution of a patient's tissue is needed or desirable, including but not limited to a patient's dura mater.

The implant of the present disclosure comprises a porous layer, a first and a second hydrogel precursors and may optionally comprise one or more additional layers.

Figure 1:
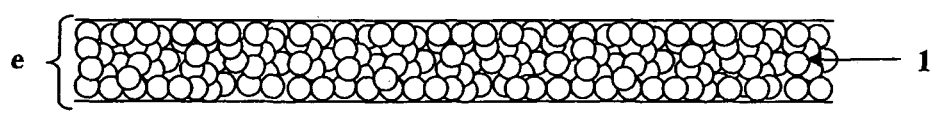
FIG. 1 schematically illustrates a monolayer implant in accordance with an embodiment of the present disclosure.

In embodiments, the present tissue patch includes a porous matrix (1) containing the first and second hydrogel precursors as shown schematically in FIG. 1. There are no films or non-porous layers in such embodiments. In embodiments, the porous layer includes two sublayers to help ensure that the first and second hydrogel precursors are physically separated prior to implantation. Thus, the porous layer may include a first sublayer containing the first hydrogel precursor and a second sublayer containing the second hydrogel precursor. These embodiments are described in more detail below.

Figure 2:
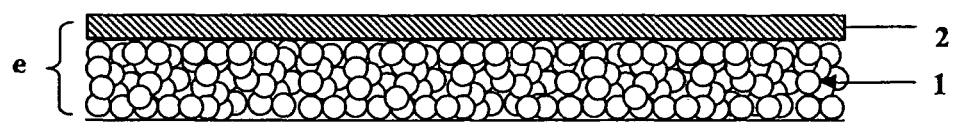
FIG. 2 schematically illustrates a two layer implant in accordance with an embodiment of the present disclosure.

In other embodiments, the present implants are bi-component layered structures shown schematically in FIG. 2 as including a porous matrix (1) loaded with a first hydrogel precursor (2) and a second layer directly spread onto the porous layer or a porous sublayer thereof, and made from a composition containing a second hydrogel precursor. To help keeping the first and second hydrogel precursors from contacting each other prior to implantation, the portion of the porous layer onto which the second hydrogel precursor is applied, which may be a sublayer of said porous layer, can be free of any hydrogel precursor.

Figure 3:
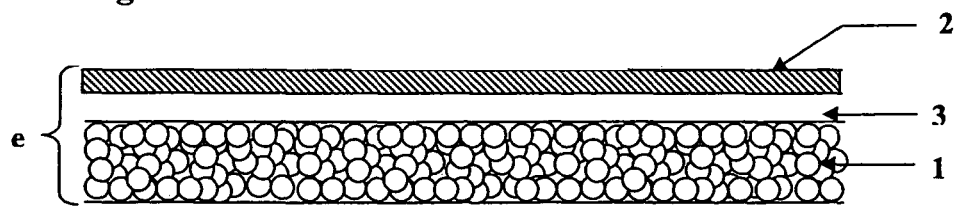
FIG. 3 schematically illustrates a three layer implant in accordance with an embodiment of the present disclosure.

In other embodiments, the present implants are tri-component layered structures shown schematically in FIG. 3 as including a porous matrix (1), and a first non porous layer (3) directly spread onto the porous layer. Either the porous or the non porous layer can contain a first hydrogel precursor. A third layer (2) made from a composition containing a second hydrogel precursor is spread directly onto the first non-porous layer.

In embodiments, the thickness (for example, as indicated by "e" in FIGS. 1-3) of the fully processed implant, in the dry state, is in the range of about 0.2 mm to about 1 cm.

In embodiments, the first hydrogel precursor is spatially separated from the second hydrogel precursor to prevent hydrogel precursors from reacting with each other until the implant is placed at the site of implantation and exposed to the physiological fluids of a patient.

During use, the implant can be oriented differently depending on the size of the defect (see FIG. 9A). In the cases of small defects the non-porous layer containing one of the hydrogel precursors is applied closer to the tissue and the porous matrix of the implant containing the other hydrogel precursor is positioned further from the tissue. This first case will create a watertight barrier over the defect to avoid any leakage of physiological fluid (e.g., CSF) supported by a backing material providing a longer tissue support after the sealant will be degraded.

In the cases of bigger defects (see FIG. 9B) the portion of the porous matrix containing one of the hydrogel precursors is applied closer to the tissue and the layer of the implant containing the other hydrogel precursor is positioned further from the tissue. This second case will first bring the porous matrix directly onto the defect to support the tissue regeneration while the hydrogel barrier will be located over the matrix closing the defect but leaving free access for cell and tissue growth through the matrix.

Upon contact with tissue, such as, for example, dural defect, the implant will soak up physiological fluid and the second hydrogel precursor will be dissolved by the fluid. As the fluid wicks into and migrates across the implant, it will carry the dissolved second hydrogel precursor along through the implant. Eventually, the fluid will migrate through the implant sufficiently to reach the portion to which the first hydrogel precursor is applied, thereby dissolving the first hydrogel precursor. The first and second hydrogel precursors will then react to form a biocompatible cross linked material, thereby assisting sticking the patch and sealing the dural defect. The biocompatible cross linked material produced by reaction of the first and second hydrogel precursors not only stickiness and sealant properties but also provide the implant with anti-adhesive properties between brain and neo-dura mater.

Collagen and its Derivatives

Collagen is a naturally occurring protein exhibiting good biocompatibility. It is the major structural component of vertebrates, forming extracellular fibers or networks in practically every tissue of the body, including skin, bone, cartilage, and blood vessels. In medical devices, collagen provides a more physiological, isotropic environment that has been shown to promote the growth and function of different cell types, facilitating the rapid overgrowth of host tissue after implantation.

For the purpose of the present application, the term "collagen" is intended to mean any known collagen of porcine, bovine or human origin, including both natural or recombinant collagen, esterified collagen, for example methylated, ethylated or alternatively succinylated collagen, glycosylated collagen (e.g., collagen glycosylated with free amino saccharides/polysaccharides, collagen glycosylated with saccharides/polysaccharides comprising vicinal diols, collagen glycosylated with saccharides/polysaccharides comprising —$CH_x(NH_2)$—$CH_y(OH)$— chemical bonds), or one of its derivatives.

The term "gelatine" here includes commercial gelatine made of collagen which has been denatured by heating and in which the chains are at least partially hydrolyzed (molecular weight lower than 100 kDa).

The collagen used can be of human or animal origin. Some non-limiting examples include, type I porcine or bovine collagen, type I or type III human collagen or mixtures in any proportions of these types. In embodiments, the collagen or gelatine used is a porcine collagen.

The collagen can be functionalized by using any method known to those skilled in the art to provide pendant portions of the collagen with moieties which are capable of covalently bonding with the amino groups of a polymer such as collagen itself including its derivatives or modified glycosaminoglycan. Examples of such pendant moieties include aldehyde groups, sulfone groups, vinylsulfone groups, isocyanate groups, acid anhydride groups, epoxide groups, aziridine groups and episulfide groups. In addition, electrophilic groups such as —CO$_2$N(COCH$_2$)$_2$, —CO$_2$N (COCH$_2$)$_2$, —CO$_2$H, —CHO, —CHOCH$_2$, —N=C=O, —SO$_2$CH=CH$_2$, —N(COCH)$_2$, —S—S—(C$_5$H$_4$N) may also be added to pendant chains of the collagen to allow covalent bonding to occur with the natural polymer showing amino group on their chains. Other suitable functional groups which may be added to collagen include groups of the following structures wherein X is Halogen and R is hydrogen or C$_1$ to C$_4$ alkyl:

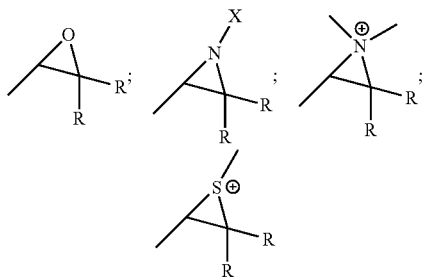

In embodiments, the collagen may be modified through the addition of an oxidizing agent. Contacting collagen with an oxidizing agent creates oxidative cleavage along portions of the collagen thereby creating pendant aldehyde groups capable of reacting with the glycosaminoglycans. The oxidizing agent may be, for example, iodine, peroxide, periodic acid, hydrogen peroxide, a periodate, a compound containing periodate, sodium periodate, a diisocyanate compound, a halogen, a compound containing halogen, n-bromosuccinimide, a permanganate, a compound containing permanganate, ozone, a compound containing ozone, chromic acid, sulfuryl chloride, a sulfoxide, a selenoxide, an oxidizing enzyme (oxidase) and combinations thereof. In embodiments, the oxidizing agent is periodic acid.

Oxidized collagen can be fully degraded in vivo, after few weeks. It is obtained by the oxidation of a 3% (w/w) collagen solution by periodic acid (C=8 mM) at room temperature, during 3 hours. An example of the oxidative technique is described by Tardy et al. in U.S. Pat. No. 4,931,546, the entire content of which is herein incorporated by reference. Another technique for oxidized collagen is by oxidation of a 3% collagen solution by periodic acid, at a final concentration of 8 mM, during 3 hours, as described in U.S. Pat. No. 6,596,304, the entire content of which is herein incorporated by reference.

Oxidation of collagen forms aldehydes groups which allow cross-linking of the collagen with the amino groups of the chitosan. The cross-linked blend chitosan/collagen is less prone to the enzymatic degradation and then has a longer time of bioresorption in-vivo. Moreover the covalent bonds generated by the cross-linking decrease the solubility of the material in water at physiological pH and allow the formation of a tri-dimensional network which is a support for cell growth and differentiation and then tissue regeneration.

Glycosaminoglycans and their Derivatives

The term "glycosaminoglycan" is intended to encompass complex polysaccharides having repeating units of either the same saccharide subunit or two or more different saccharide subunits. Some non-limiting examples of glycosaminoglycans include dermatan surfate, hyaluronic acid, the chondroitin sulfates, chitin, heparin, keratan surfate, keratosulfate, and derivatives thereof. Some non-limiting examples of derivatives may include partially and fully deacetylated versions of these compounds such as chitosan and deacetylated hyaluronic acid. The glycosaminoglycans may be extracted from a natural source, e.g., animal tissues such as squid pens and shrimp shells or vegetable sources such as mushrooms (e.g., "champigon de paris"), or they may be synthetically produced or synthesized by modified microorganisms such as bacteria.

In embodiments, the functionalized collagen may be combined with a glycosaminoglycan such as chitosan to crosslink and form covalent bonds. The glycosaminoglycan displays a degree of acetylation (DA) of about 0% to about 60%. In embodiments, the glycosaminoglycan displays a degree of acetylation (DA) of about 1% to about 50%. Samples of different degrees of acetylation can be obtained either by a heterogeneous deacetylation process or by a homogenous reacetylating process from a sample of a glycosaminoglycan that is fully deacetylated.

In embodiments, the glycosaminoglycan has a molecular weight ranging from about 100 to about 3,000,000 g/mol. In some embodiments, the glycosaminoglycan has a molecular weight ranging from about 164 (chitosan monomer) to about 1,000,000 g/mol. In addition, the glycosaminoglycan also displays a low polydispersity index between about 1.2 to about 2. In particularly useful embodiments, the glycosaminoglycan is chitosan. Nevertheless, the glycosaminoglycan may be a mixture of chitosans with different degrees of acetylation or a mixture of chitosans and other glycosaminoglycans, e.g. hyaluronic acid, with different degrees of acetylation and in which all glycosaminoglycan have the capability, i.e. have free amino groups, to be cross-linked to the oxidized collagen.

First and Second Hydrogel Precursors

The terms "first hydrogel precursor" and "second hydrogel precursor" each means a polymer, functional polymer, macromolecule, small molecule, or crosslinker that can take part in a reaction to form a network of crosslinked molecules, e.g., a hydrogel.

In embodiments, at least one of the first or second hydrogel precursors is a small molecule of about 1000 Da or less, and is referred to as a "crosslinker". The crosslinker preferably has a solubility of at least 1 g/100 mL in an aqueous solution. A crosslinked molecule may be cross-linked via an ionic or covalent bond, a physical force, or other attraction.

In embodiments, at least one of the first or second hydrogel precursors is a macromolecule, and is referred to as a "functional polymer". The macromolecule, when reacted in combination with a crosslinker, is preferably at least five to fifty times greater in molecular weight than the small molecule crosslinker and can be less than about 60,000 Da. In embodiments, a macromolecule that is seven to thirty times greater in molecular weight than the crosslinker is used and, in embodiments a macromolecule that is about ten to twenty times difference in weight is used. Further, a macromolecular molecular weight of 5,000 to 50,000 is useful. The term polymer, as used herein, means a molecule formed of at least three repeating groups.

Each of the first and second hydrogel precursors is multifunctional, meaning that it comprises two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form crosslinked polymeric products. Such reactions are referred to as "crosslinking reactions".

In embodiments, each of the first and second hydrogel precursors includes only one category of functional groups, either only nucleophilic groups or only electrophilic functional groups, so long as both nucleophilic and electrophilic precursors are used in the crosslinking reaction. Thus, for example, if the first hydrogel precursor has nucleophilic functional groups such as amines, the second hydrogel precursor may have electrophilic functional groups such as N-hydroxysuccinimides. On the other hand, if the first hydrogel precursor has electrophilic functional groups such as sulfosuccinimides, then the second hydrogel precursor may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second hydrogel precursors may have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxyethylcellulose, hyaluronic acid, and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second hydrogel precursors water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

If it is desired that the biocompatible crosslinked polymer resulting from the reaction of the first and second hydrogel precursors be biodegradable or absorbable, one or more of the first and second hydrogel precursors may have biodegradable linkages present between the functional groups. The biodegradable linkage optionally also may serve as the water soluble core of one or more of the precursors. In the alternative, or in addition, the functional groups of the first and second hydrogel precursors may be chosen such that the product of the reaction between them results in a biodegradable linkage. For each approach, biodegradable linkages may be chosen such that the resulting biodegradable biocompatible crosslinked polymer will degrade, dissolve or be absorbed in a desired period of time. Preferably, biodegradable linkages are selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, dl-lactide, l-lactide, caprolactone, dioxanone, and tritnethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(amino acids), poly(carbonate)s, poly(saccharide)s and poly(phosphonate)s.

In embodiments, the biodegradable linkage may contain ester linkages. Some non-limiting examples include esters of succinic acid, glutaric acid, propionic acid, adipic acid, or amino acids, as well as carboxymethyl esters.

In embodiments, a multifunctional nucleophilic polymer such as trilysine may be used as a first hydrogel precursor and a multifunctional electrophilic polymer such as a multi-arm PEG functionalized with multiple NHS groups may be used as a second hydrogel precursor. The multi-arm PEG functionalized with multiple NHS groups can for example have four, six or eight arms and have a molecular weight of from about 5,000 to about 25,000. Many other examples of suitable first and second precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

The first hydrogel precursor may be applied to a first portion of the porous substrate and a second hydrogel precursor may be applied to a second portion of the porous substrate. For example, the precursors may be applied in a dry form, such as particulate matter or in a solid or semi-solid state such as a film, or foam. In embodiments, at least one of the first or second hydrogel precursors is applied to the porous matrix as a film. In embodiments, the first portion of the substrate having the first hydrogel precursor applied thereto is spatially separated from the second portion of the porous substrate having the second hydrogel precursor applied thereto. Having the first and second hydrogel precursors spatially separated from each other prevents them from reacting with each other until the implant is placed at the site of implantation and exposed to the physiological fluids of a patient.

Porous Layer

The porous layer or matrix can be obtained by freeze-drying a polymer solution containing one or more biodegradable and biocompatible polymers. Table 1 shows illustrative embodiments of polymer solutions suitable for use in forming the porous layer using a freeze-drying process.

TABLE 1

| | |
|---|---|
| (A) chitosan content | 0%--99% (w/w) |
| (B) Oxidized collagen content | 100%--1% (w/w) |
| Total polymer concentration in the suspension | 0.2%--5% (w/w) |

Where both chitosan and collagen are used, the weight ratio of chitosan to collagen in the composition used to form the porous layer may be from about 1:100 to 100:1, in embodiments, the weight ratio of chitosan to collagen is from about 1:10 to about 10:1, in yet other embodiments, the weight ratio of chitosan to collagen is about 1:1.

In embodiments, the composition from which the porous layer is formed contains from about 40 to about 95 percent by weight chitosan and from about 5 to about 60 percent by weight functionalized collagen. In embodiments, the total polymer concentration in the suspension used to form the porous layer is from about 0.5% w/w to about 2% w/w.

Combining Collagen and Glycosaminoglycan to Form the Porous Layer

Compounds useful in forming the porous layer of the implant of the present disclosure can be made by reacting a functionalized collagen with a glycosaminoglycan under conditions which cause the two components to self-cross link. As used herein, the term "self-crosslinked" when used in connection with the crosslinking of polymers means that two or more polymers are covalently bonded together by functionalities present on the polymers themselves without the use of a chemical cross linking agent. As an illustrative example, oxidized collagen (which contains aldehyde groups thereon) will covalently bond to chitosan (which contains amino groups thereon) without the addition of any separate chemical crosslinking agent to form a self-crosslinked compound. The two components may take the form of any solution, suspension, emulsion, semi-solid, or solid material capable of allowing the two-components to interact and self-crosslink.

In embodiments, each component is solubilized in an acceptable solvent such as deionized water to form two separate solutions. The two solutions may be combined to allow the two components to mix, self-crosslink and form the compounds described herein. In particular embodiments, the glycosaminoglycan is solubilized in deionized water with a stoichiometric amount of acid with a polymer concentration ranging from about 0.5% to about 10% (w/w). It is envisioned that the pH of the glycosaminoglycan solution can be adjusted if necessary between about 2 and about 7.5 depending on the degree of acetylation. The functionalized collagen is also solubilized in an acceptable solvent such as deionized water to a concentration ranging from about 0.5% to about 10% (w/w). It is also envisioned that the pH of the functionalized collagen solution may be adjusted between about 2 and about 7.5. The two components in solution are mixed to a final concentration of polymer comprising 0.5% and 20% (w/w). In embodiments, different proportions between the functionalized collagen and the glycosaminoglycan may be used. In particular embodiments, the glycosaminoglycan may be composed of a mixture of chitosans with different degrees of acetylation (DA). The chitosan having a degradation time in function with its degree of acetylation (Kurita et al., Carbohydrate polymers. Vol 42 pp. 19-21,200; Tomihata et al., Biomaterials. Vol 18 n° 7 pp. 567-575, 1997), the combination of slow and fast biodegradable chitosan is advantageous, for example, for progressive cell colonization of the porous layer. In fact, the degradation of the slow biodegradable oxidized collagen and chitosan with high DA, i.e. $35 \leq D\ A \leq 50$, in vitro in the presence of viable cells and in vivo, helps to increase the interconnected porosity assisting in the regeneration of healthy native like tissue in the full thickness of the implant and the extent of tissue integration. In embodiments, molecules released from the controlled degradation of the biocomposite, for example oxidized collagen/chitosan, may advantageously confer to the implant highly interesting biological activities e.g. antimicrobial, anticancer, antioxidant, and immunostimulant effects, especially in the case of chitosan (Kim et al., Carbohydrate Polymers, Vol. 62, Issue 4, pp. 357-368, 2005) and may bring, in complement of the biocompatibility and biodegradability, bioactive properties to the medical devices. The biological properties of released chitosan oligopolymers enhance the tissue regeneration and extend the use of the implant, for example, to surgical sites with a high risk of contamination.

In embodiments, a combination of two solutions comprising an acidic solution of oxidized collagen and an acidic solution of chitosan with one or a mixture of several degrees of acetylation is used. The collagen is oxidized by the addition of periodic acid as the oxidizing agent and the chitosan solution is made acidic by the addition of hydrochloric acid. The mixture can be neutralized either with an alkaline vapour/solution or buffer solution with a pH greater than 7, leading to a cross-linked scaffold compatible for cell adhesion and proliferation.

Optionally, glycerine may be added to the solution used to form the porous layer. When present, the concentration of glycerine in the solution can typically be from about 2 to about 10 times less than that of the combined amount of collagen and glycosaminoglycan, in embodiments less than about one-third of the combined amount of collagen and glycosaminoglycan.

In embodiments, the first hydrogel precursor is loaded in the porous layer by incorporating the precursor in the polymer solution before freeze-drying. However where it is desired to segregate the first and the second hydrogel precursor the matrix bulk can be designed to preserve a volume free of both hydrogel precursors between the first portion with first hydrogel precursor and second portion with second hydrogel precursor as described in more detail below in connection with, for example, FIGS. 7A-D.

The porous layer can be from about 0.1 mm to about 10 mm thick in the dry state. In multi-layer embodiments, the porous layer can be from about 0.2 mm to about 5 mm thick in the dry state. The porous layer displaying such a thickness can have a density of from about 0.1 mg polymers (e.g., collagen and glycosaminoglycans) for each square centimeter (length×width of the porous layer) to about 50 mg polymers for each square centimeter, in embodiments from about 0.25 mg polymers for each square centimeter to about 20 mg polymers for each square centimeter. The size of the pores in such a porous layer can be from about 10 µm to about 1000 µm, in embodiments from about 50 µm to about 500 µm.

After formation, the porous matrix can be compacted by using a press or any other appropriate means.

The Non-Porous Layer

When present, the non porous layer used in the implants of the present disclosure can be a collagen film. Suitable collagen films can be made from non heated oxidized collagen or a blend of heated oxidized collagen and non oxidized heated collagen or combinations thereof. If heated oxidized collagen is used, the formulation of the film can be the formulations disclosed in U.S. Pat. No. 6,596,304, the entire disclosure of which is incorporated herein by reference.

Any materials which may enhance tissue repair, limit the risk of sepsis and modulate the mechanical properties (e.g., glycerol, 1-2 propandiol) of the film (swelling rate in water, tensile strength and the like) may be added during the preparation or in the film formulation.

The film may be further cross-linked by any known methods, when dried or during its drying.

Table 2 gives illustrative concentrations of collagen solutions useful in forming the non-porous layer.

TABLE 2

| | |
|---|---|
| Non heated oxidized collagen content | 0.1%--3% (w/w) |
| Heated Oxidized collagen content | 0.1%--6% (w/w) |
| Heated collagen content | 0.1%--6% (w/w) |

The non-porous layer may be prepared by pouring a collagen-containing solution onto a substantially flat support and distributing it evenly. This solution is left to gel by the removal of solvent and cooling.

Examples of solutions useful in forming the non-porous layer include from about 0.1 to about 3% w/w of non-heated oxidised collagen, up to 2% w/w polyethylene glycol and up to 1% w/w glycerol. In embodiments, solutions useful in forming the non-porous layer include from about 0.5 to about 1.5% w/w of non-heated oxidised collagen, from about 0.6 to about 0.9% w/w polyethylene glycol and from about 0.3 to about 0.6% w/w glycerol.

In the dry state, the resulting non-porous layer may contain from about 40 to about 100% w/w of non-heated oxidised collagen, up to 60% w/w polyethylene glycol and up to 20% w/w glycerol. In embodiments, the resulting non-porous layer contains from about 60 to about 90% w/w of non-heated oxidised collagen, from about 15 to about 30% w/w polyethylene glycol and from about 5 to about 15% w/w glycerol.

Other examples of solutions useful in forming the non-porous layer include from about 0.1 to about 3% w/w of heated oxidised collagen, from about 0.1 to about 3% w/w of heated collagen, up to 2% w/w polyethylene glycol and up to 1% w/w glycerol. In embodiments, solutions useful in forming the non-porous layer include from about 0.5 to about 1.5% w/w of non-heated oxidised collagen, from about 0.5 to about 1.5% w/w of heated collagen, from about 0.6 to about 0.9% w/w polyethylene glycol and from about 0.3 to about 0.6% w/w glycerol.

In the dry state, the resulting non-porous layer may contain from about 40 to about 100% w/w of heated oxidised collagen, about 40 to about 100% w/w of heated collagen, up to 60% w/w polyethylene glycol and up to 20% w/w glycerol. In embodiments, the resulting non-porous layer contains from about 60 to about 90% w/w of heated oxidised collagen, from about 60 to about 90% w/w of heated collagen, from about 15 to about 30% w/w polyethylene glycol and from about 5 to about 15% w/w glycerol.

In embodiments, at least one macromolecular hydrophilic additive that is chemically unreactive with the collagen may be added to the solution used to form the non-porous layer. "Chemically unreactive with the collagen" as used herein means a hydrophilic compound which is not likely to react with the collagen, notably which does not form covalent bonds with it during cross-linking.

The macromolecular hydrophilic additive advantageously has a molecular weight in excess of 3,000 Daltons, in embodiments from about 3,000 to about 20,000 Daltons. Illustrative examples of suitable macromolecular hydrophilic additives include polyalkylene glycols (such as polyethylene glycol), polysaccharides (e.g., starch, dextran and/or cellulose), oxidized polysaccharides, and mucopolysaccharides. It should of course be understood that combinations of macromolecular hydrophilic additives may be used. The concentration of hydrophilic additive(s) can typically be from about 2 to about 10 times less than that of the collagen.

Typically, the macromolecular hydrophilic additive is eliminated by diffusion through the non-porous layer, in a few days. The swelling of this material may advantageously promote degradation of a collagenic non-porous layer in less than a month.

Optionally, glycerine may be added to the solution used to form the non-porous layer. When present, the concentration of glycerine in the solution can typically be from about 2 to about 10 times less than that of the collagenic constituent, in embodiments less than about one-third of the collagen concentration.

The thickness of the non-porous layer is not critical, but typically can be less than about 100 μm thick, and in embodiments from about 30 μm to about 75 μm thick.

Optional Bioactive Agents

In some embodiments, at least one bioactive agent may be combined with the present dural repair materials and/or any of the individual components (the porous layer or the optional non-porous layer or layers) used to construct the present dural repair materials. In these embodiments, the present dural repair material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present dural repair materials in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the present dural repair materials and the surrounding tissues opposite the target tissue. In addition, anti-adhesive agents may be used to prevent adhesions from forming between the present dural repair materials and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the dural repair materials of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives may be included as a bioactive agent in the dural repair materials of the present disclosure.

Other bioactive agents which may be included as a bioactive agent in the dural repair materials in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present dural repair materials include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

The following non-limiting example illustrates the preparation of dural repair materials in accordance with the present disclosure.

EXAMPLES

Example 1a

Figure 4A:
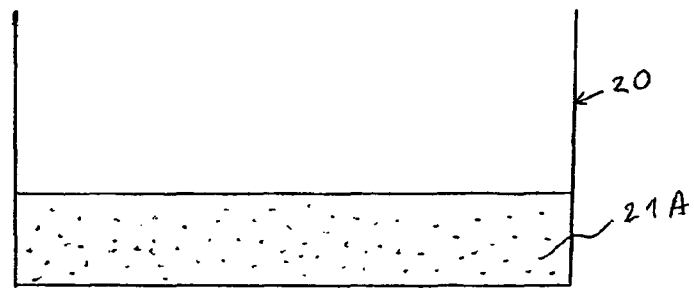
FIGS. 4A through 4D schematically illustrate a method of forming a dural implant in accordance with an embodiment of the present disclosure.
Figure 4B:
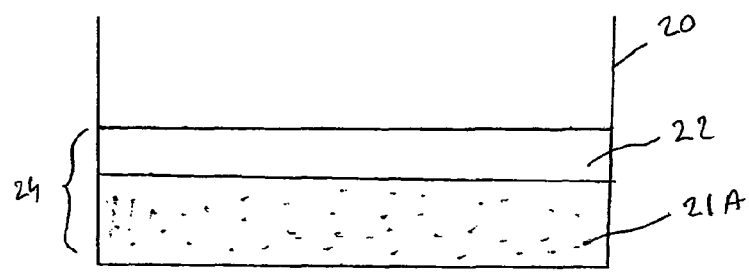
Figure 4C:
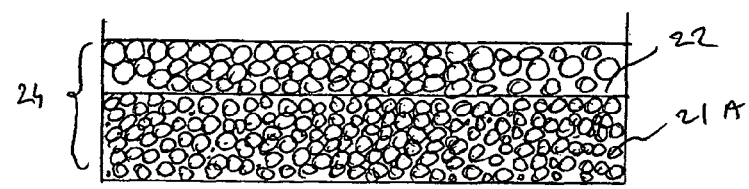
Figure 4D:
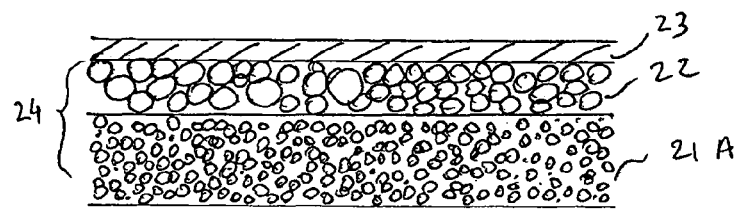

FIGS. 4A-4D illustrate a structure for an implant of the present disclosure wherein a first hydrogel precursor is mixed within a polymer solution, with a polymer concentration C1, to form a first sublayer 21A of the porous matrix 24 in container 20. The pH of the polymer/hydrogel precursor blend can be adjusted between 7 and 10 in order to allow an optimal reactivity of both hydrogel precursors, ie first hydrogel precursor and second hydrogel precursor as will be described below: nevertheless if the blend does not permit pH adjustment, a further step, described later, can be added in the process after freeze drying step. In FIG. 4B, a second solution 22, with polymer concentration C2 greater than C1, is poured over the first solution layer 21A which has been beforehand at least partially gelated or frozen. The two sublayers (21A, 22) of the porous matrix 24 are freeze dried as shown in FIG. 4C and the second hydrogel precursor 23 is spread over the sublayer 22 by coating or spraying methods as shown in FIG. 4D. If necessary, before coating, porous matrix 24 may be neutralized using a basic solution/vapour or buffer solution in order that the dissociation state of the first hydrogel precursor will be adapted for optimal reactivity with the second hydrogel precursor.

Example 1b

Alternatively, FIGS. 4A-4D may illustrate a structure for an implant of the present disclosure wherein a first hydrogel precursor is mixed within a polymer solution, with a polymer concentration C1, to form a first sublayer 21A of the porous matrix 24 in container 20, wherein the concentration C2 is lower than C1. The pH of the polymer/hydrogel precursor blend can be adjusted between 7 and 10 in order to allow an optimal reactivity of both hydrogel precursors, ie first hydrogel precursor and second hydrogel precursor as will be described below: nevertheless if the blend does not permit pH adjustment, a further step, described later, can be added in the process after freeze drying step. In FIG. 4B, a second solution 22, with polymer concentration C2 lower than C1, is poured over the first solution layer 21A. The difference of viscosity of the two solutions 21A and 22 avoids the mixing of the two different layers to preserve the bilayered structure. The two sublayers (21A, 22) of the porous matrix 24 are simultaneously freeze dried as shown in FIG. 4C and the second hydrogel precursor 23 is spread over the sublayer 22 by coating or spraying methods as shown in FIG. 4D. If necessary, before coating, porous matrix 24 may be neutralized using a basic solution/vapour or buffer solution in order that the dissociation state of the first hydrogel precursor will be adapted for optimal reactivity with the second hydrogel precursor.

Preparation of the Porous Matrix (24) Illustrating Example 1b Above

Layer 21A:

40.5 g of chitosan solution (DA 2.5%) and 40.5 g of non heated, oxidized collagen (also referred to as CXN hereinafter) solution (1% w/w) are mixed at pH 3.5 under stirring for 10 minutes. The pH of the solution is adjusted to 4.5 and tri-lysine is added to the blend as the first hydrogel precursor with a concentration of 3 mg/ml. Finally the solution is centrifuged. The solution is poured in box in order to form the sublayer 21A.

Layer 22:

Then, 20 g of chitosan solution (DA 2.5%) and 20 g of CXN solution (0.5% w/w) are mixed at pH 3.5. In sublayer 22, the concentration in CXN is therefore lower than in sublayer 21A. This lower concentration solution is gently applied over the sublayer 21A and the whole is further lyophilized. The total lyophilization time is from 18 to 72 hours.

Then the porous matrix is neutralized within water/alcohol mixture 5/95 w/w with sodium hydroxide 0.5N for 5 min and freeze dried again. As appears from the preparation method described above, sublayer 22 contains no hydrogel precursor.

Coating of the Matrix with Second Hydrogel Precursor:

A thin uniform layer of melting PEG-succinimidyl glutarate (the second hydrogel precursor) with a density of 15 mg/cm$^2$ is formed on hot surface at the temperature of 50° C. Then the sublayer 22 of the porous matrix produced above is directly applied on the melted PEG. The whole is exposed to a stream of sterile air at ambient temperature for 15 min.

The resulting implant comprises a porous layer (24), a first hydrogel precursor (tri lysine), a second hydrogel precursor (PEG-succinimidyl glutarate), wherein the first hydrogel precursor is present in the porous layer and the second hydrogel precursor is present in an additional layer, which is a non porous layer.

In particular, the resulting implant comprises a porous layer having a first sublayer 21A comprising a first hydrogel precursor and a second sublayer 22 free from hydrogel precursor, and a thin layer containing a second hydrogel precursor applied to the second sublayer free from hydrogel precursor. The first and second hydrogel precursors are therefore spatially separated.

When implanted at the site of a dural defect the first and second hydrogel precursors of the present implant are activated by the body fluids to induce in situ formation of a hydrogel providing both stickiness and sealing properties to the implant.

Example 1c

Figure 5A:
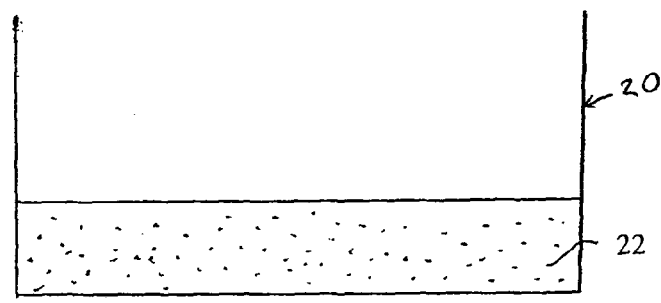
FIGS. 5A through 5D schematically illustrate a method of forming a dural implant in accordance with another embodiment of the present disclosure.
Figure 5B:
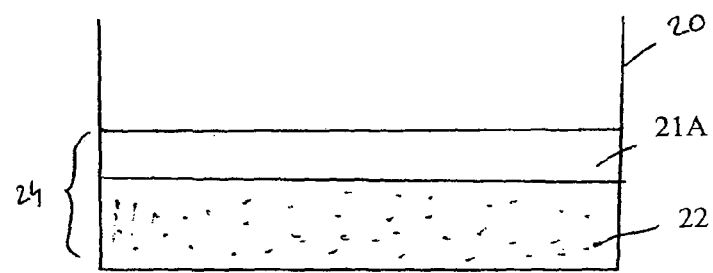
Figure 5C:
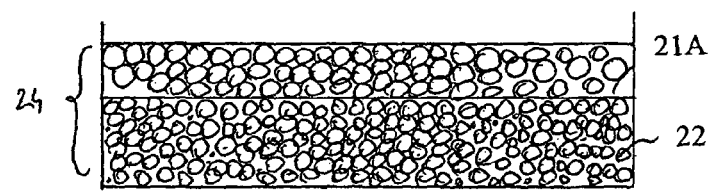
Figure 5D:
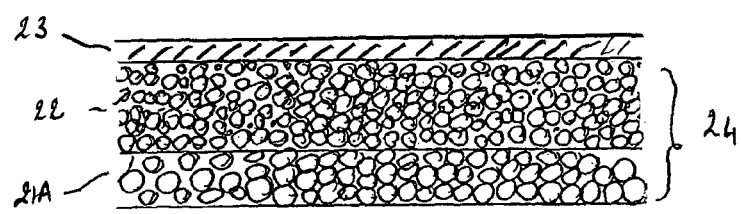
Figure 6A:
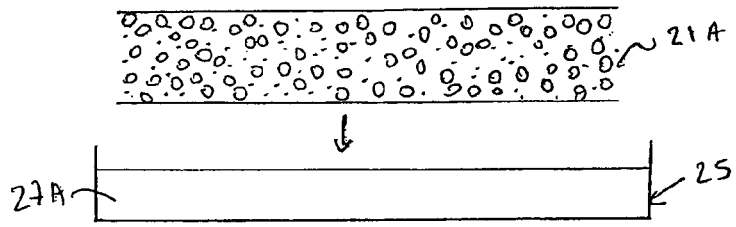
FIGS. 6A through 6D schematically illustrate a method of forming a dural implant in accordance with an alternative embodiment of the present disclosure.
Figure 6B:
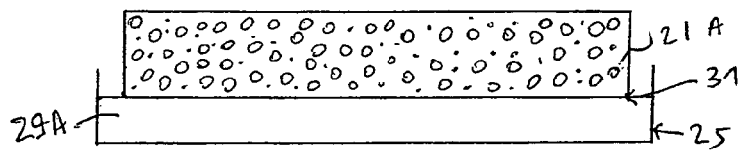
Figure 6C:
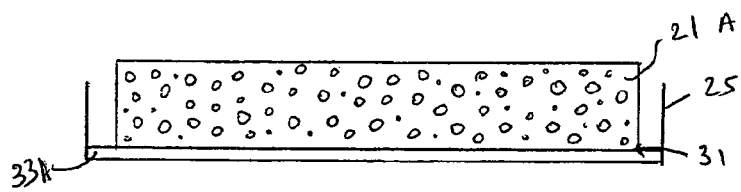
Figure 6D:
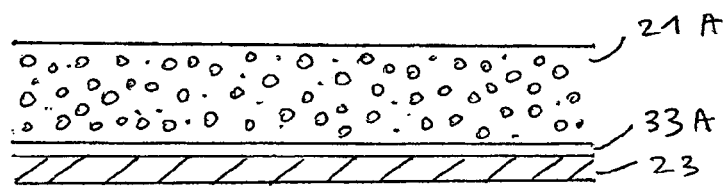
Figure 7A:
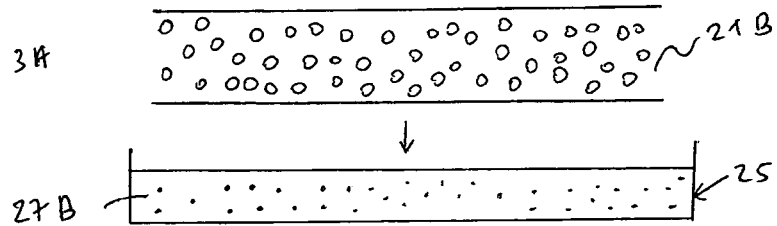
FIGS. 7A through 7D schematically illustrate a method of forming a dural implant in accordance with yet another embodiment of the present disclosure.
Figure 7B:
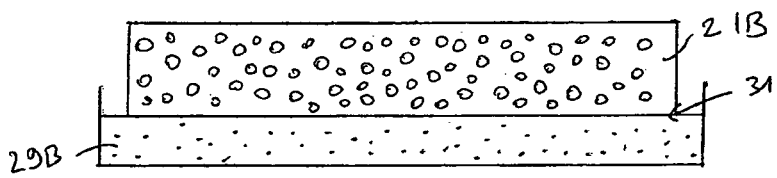
Figure 7C:
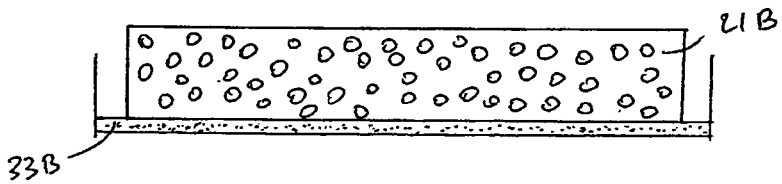
Figure 7D:
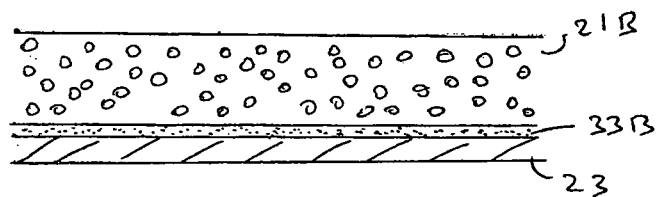

FIGS. 5A-5D illustrate a structure for an implant of the present disclosure, wherein a first polymer solution, with a polymer concentration C1, forms a first sub layer 22 of the porous matrix 24 in container 20. In FIG. 5B, a second solution 21A wherein a first hydrogel precursor is mixed within a polymer solution, with polymer concentration C2 lower than C1, is poured over the first solution layer 22. The pH of the polymer/hydrogel precursor blend can be adjusted between 7 and 10 in order to allow an optimal reactivity of both hydrogel precursors; nevertheless if the blend does not permit pH adjustment a further step, described later, can be added in the process after freeze drying step. The difference of viscosity of the two solutions 21A and 22 avoids the mixing of the two different layers to preserve the bilayered structure The two sublayers (22, 21A) of the porous matrix 24 are freeze dried as shown in FIG. 5C and the second hydrogel precursor 23 is spread over the sublayer 22 by coating or spraying methods as shown in FIG. 5D. If necessary, before coating, porous matrix 24 may be neutralized using a basic solution/vapour or buffer solution in order that the dissociation state of the first hydrogel precursor will be adapted for optimal reactivity with the second hydrogel precursor.

Preparation of the Porous Matrix (24) Illustrating Example 1c

Layer 22:

20 g of chitosan solution (DA 2.5%) and 20 g of non heated, oxidized collagen solution (2% w/w) are mixed at pH 3.5 under stirring for 10 minutes. The pH of the solution is adjusted to 4.5. Finally the solution is centrifuged and poured in the box in order to form the sublayer 22. Sublayer 22 is free of hydrogel precursor.

Layer 21A:

Then, 40.5 g of chitosan solution (DA 2.5%) and 40.5 g of CXN solution (0.8% w/w) are mixed at pH 3.5 and tri-lysine is added as a first hydrogel precursor to the blend with a concentration of 3 mg/ml. In sublayer 21A, the concentration in CXN is lower than in sublayer 22. This lower concentration solution is gently applied over the sublayer 22 and the whole is further lyophilized. The total lyophilization time is from 18 to 72 hours.

Then the porous matrix is neutralized within water/alcohol mixture 5/95 w/w with sodium hydroxide 0.5N for 5 min and freeze dry again.

Coating of the Matrix with Second Hydrogel Precursor:

A thin uniform layer of melting PEG-succinimidyl glutarate (the second hydrogel precursor) with a density of 15 mg/cm$^2$ is formed on hot surface at the temperature of 50° C. Then the sublayer 22 of the porous matrix produced above is directly applied on the melted PEG. The whole is exposed to a stream of sterile air at ambient temperature for 15 min.

The resulting implant comprises a porous layer having a first sublayer 21A comprising a first hydrogel precursor and a second sublayer 22 free from hydrogel precursor, and a thin layer containing a second hydrogel precursor applied to the second sublayer free from hydrogel precursor. The first and second hydrogel precursors are therefore spatially separated.

When implanted at the site of a dural defect the first and second hydrogel precursors of the present implant are activated by the body fluids to induce in situ formation of a hydrogel providing both stickiness and sealing properties to the implant.

Example 2

In FIGS. 6A-6D a sequence is shown wherein a preformed porous layer 21A containing a first hydrogel precursor is applied to a gelling layer 29A formed from a solution layer 27A poured in a container 25. During a solvent casting step, 21A is at least partially impregnated of 29A forming a transition 31. After complete drying of layer 29A, porous layer 21A and non-porous layer 33A, resulting from the drying of layer 29A, are well associated. Then the second hydrogel precursor is spread onto 33A to form a layer 23. As in FIG. 4A-4D, the porous matrix loaded with first hydrogel precursor 21A can be neutralized as previously described.

Preparation of the Porous Matrix (21A)

60.5 g of chitosan solution (DA 2.5%) and 60.5 g of non heated, oxidized collagen solution (1% w/w) are mixed at pH 3.5 under stirring for 10 minutes. The pH of the solution is adjusted to 4.5 and tri-lysine is added to the blend as a first hydrogel precursor with a concentration of 3 mg/ml. Finally the solution is centrifuged, applied within desire box size and further lyophilized. The total lyophilisation time is from 18 to 72 hours.

Then the porous matrix is neutralized within water/alcohol mixture 5/95 w/w with sodium hydroxide 0.5N for 5 min and freeze dried again.

Application of a Film (33A) to One Face of the Implant

The porous matrix (21A) obtained above is subsequently coated with an oxidized collagen film as described in Example 2 of U.S. Pat. No. 6,391,939.

A concentrated sterile solution of PEG 4000 (polyethylene glycol having a molecular weight of 4000 D, for example sold by the company Fluka under the trade name PEG 4000) and glycerol is added to a solution of oxidized collagen (obtained by oxidation of porcine collagen) at 3% w/w, so as to obtain a final composition having a PEG 4000 concentration of 1% w/w and a glycerol concentration of 0.6% w/v. The pH of the solution is adjusted to 7.0 by adding a concentrated solution of sodium hydroxide. The volume of the solution is then adjusted with sterile water so as to obtain final concentrations of collagen, of PEG 4000 and of glycerol of 1% w/v, 0.9% w/v and 0.54% w/v, respectively. The solution is then spread out so as to form a thin sheet, namely solution layer 27A mentioned above, with a density of 0.05 g/cm² on a flat hydrophobic support of polyvinyl chloride or polystyrene type. The surface is then exposed to a stream of sterile air at ambient temperature for at least one hour and the porous (21A) matrix obtained above is then applied carefully to the gelled layer, namely gelling layer 29A mentioned above, obtained from solution layer 27A. The whole is exposed to a stream of sterile air at ambient temperature until complete evaporation in about 18 hours, during which gelling layer 29A dries up to form film 33A. The result is a porous matrix-collagen film composite.

As mentioned above, the second hydrogel precursor is spread onto 33A to form a layer 23. The resulting implant is shown on FIG. 6D.

The first and second hydrogel precursors are therefore spatially separated.

When implanted at the site of a dural defect the first and second hydrogel precursors of the present implant are activated by the body fluids to induce in situ formation of a hydrogel providing both stickiness and sealing properties to the implant.

Example 3

In FIGS. 7A-7D a sequence is shown wherein a preformed porous matrix layer 21B free of hydrogel precursor is applied to a gelling layer 29B formed from a solution layer 27B poured in a container 25. In solution 27B, the first hydrogel precursor is added and the pH adjusted between 7 and 8. During a solvent casting step, porous layer 21B is at least partially impregnated of 29B forming a transition 31. After complete drying of gelling layer 29B, porous layer 21B and non-porous layer 33B, resulting from the drying of layer 29B are well associated. Then the second hydrogel precursor is spread onto non-porous layer 33B to form layer 23. Because 33B is dry and a non porous layer, the first and second precursor can not react during the coating deposition step.

Example 4

Figure 8A:
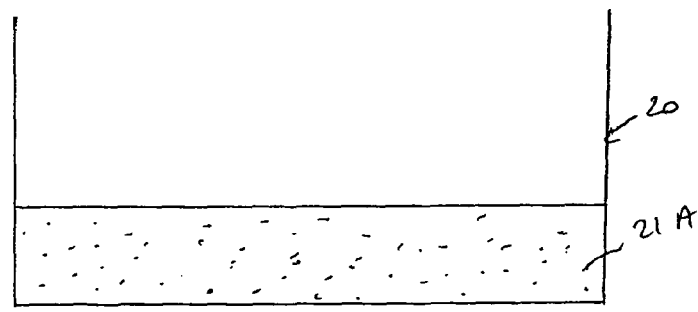
FIGS. 8A through 8D schematically illustrate a method of forming a dural implant in accordance with yet another embodiment of the present disclosure.
Figure 8B:
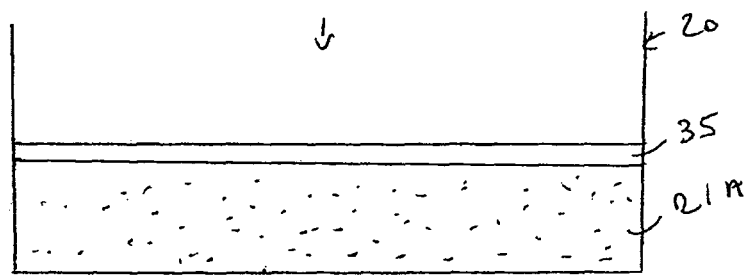
Figure 8C:
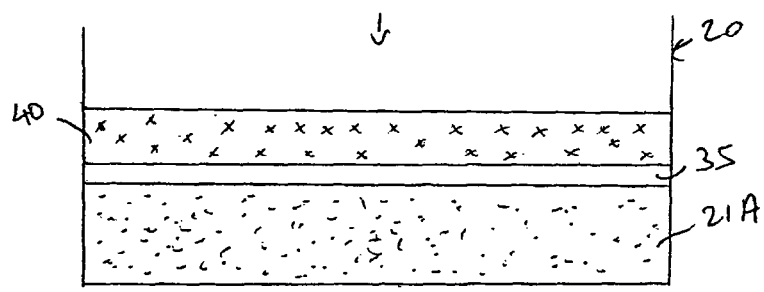
Figure 8D:
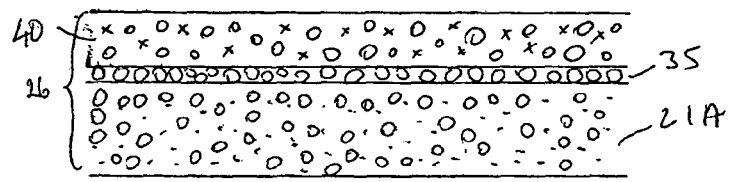

In FIGS. 8A-8D are illustrated a structure for an implant of the present disclosure wherein a first hydrogel precursor is mixed within the polymer solution, with a polymer concentration C1, to form a first sublayer 21A of the porous matrix 26 in the container 20. Preferably, the pH of the polymer/hydrogel precursor blend should be adjusted between 7 and 8 in order to allow an optimal reactivity of both hydrogel precursors, ie first hydrogel precursor and second hydrogel precursor, as described below. In FIG. 8B, a second solution 35, with a polymer concentration C2 different than C1, is poured over the first solution layer 21A which has been beforehand at least partially gelated or frozen. In FIG. 8C, a third solution 40 having a polymer concentration C3 and in which the second hydrogel precursor has been loaded is poured over solution layer 35 which has been beforehand at least partially gelated or frozen. Then, the three sublayers 26 of the porous matrix are freeze dried as shown in FIG. 8D.

The resulting implant comprises one porous layer comprising a first porous sublayer comprising a first hydrogel precursor secured to a second porous sublayer comprising a second hydrogel precursor via an intermediate porous sublayer containing no hydrogel precursor. When implanted at the site of a dural defect the first and second hydrogel precursors of the present implant are activated by the body fluids to induce in situ formation of a hydrogel providing both stickiness and sealing properties to the implant.

It will be understood that various modifications may be made to the embodiments disclosed herein. For example, more than two precursors may be applied to the porous substrate to form the hemostatic implant. As another example, the first and second precursors may each be applied to the porous substrate as a film. Thus, those skilled in the art will envision other modifications within the scope and spirit of the claims.

What is claimed is:

1. An implant comprising:
 a porous layer comprising a self-crosslinked compound comprising oxidized collagen and chitosan,
 a first additional layer,
 a second additional layer located between said porous layer and said first additional layer,
 a first hydrogel precursor present in said porous layer, and,
 a second hydrogel precursor present in said first additional layer,
 wherein said second additional layer is free of hydrogel precursor, and the first hydrogel precursor is spatially separated from the second hydrogel precursor.

2. The implant of claim 1, wherein the first hydrogel precursor comprises nucleophilic functional groups and the second hydrogel precursor comprises electrophilic functional groups.

3. The implant of claim 1, wherein the first hydrogel precursor comprises tri-lysine and the second hydrogel precursor comprises PEG-succinimidyl glutarate.

4. The implant of claim 1, wherein the chitosan comprises a degree of acetylation of about 1% to about 50%.

5. The implant of claim 1, wherein the chitosan comprises a degree of acetylation of about 2.5%.

6. The implant of claim 1, wherein said first additional layer is a non porous layer.

7. The implant of claim 6, wherein said second additional layer is a non porous layer.

8. The implant of claim 1, wherein said first additional layer is a porous layer.

9. The implant of claim 8, wherein said second additional layer is a porous layer.

* * * * *